United States Patent
Roberts et al.

(10) Patent No.: US 8,649,757 B2
(45) Date of Patent: Feb. 11, 2014

(54) PROXIMITY BASED SELECTION OF AN IMPLANTABLE MEDICAL DEVICE FOR FAR FIELD COMMUNICATION

(75) Inventors: Earle T. Roberts, Maple Grove, MN (US); Donald L. Villalta, Minneapolis, MN (US); David S Slack, Plymouth, MN (US); Irfan Z. Ali, Woodbury, MN (US); Sudheendhar Raghavendran, St. Anthony, MN (US); Nathan A. Torgerson, Andover, MN (US); Garrett R. Sipple, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

(21) Appl. No.: 12/686,971

(22) Filed: Jan. 13, 2010

(65) Prior Publication Data
US 2011/0172741 A1    Jul. 14, 2011

(51) Int. Cl.
H04M 11/04    (2006.01)
A61N 1/08    (2006.01)

(52) U.S. Cl.
USPC ......... 455/404.1; 455/41.2; 455/421; 607/30; 607/31; 607/32; 607/59; 607/60

(58) Field of Classification Search
USPC .............. 607/30–32, 59, 60; 455/404.1, 41.2, 455/421
See application file for complete search history.

(56) References Cited

U.S. PATENT DOCUMENTS

| | | | |
|---|---|---|---|
| 4,773,001 A | 9/1988 | Blair et al. | |
| 6,131,136 A | 10/2000 | Liebenow et al. | |
| 6,507,734 B1 | 1/2003 | Berger et al. | |
| 6,786,930 B2 | 9/2004 | Biscup | |
| 6,928,295 B2 | 8/2005 | Olson et al. | |
| 7,039,392 B2 | 5/2006 | McCorkle et al. | |
| 7,155,290 B2 | 12/2006 | Von Arx et al. | |
| 7,174,130 B2 | 2/2007 | Kurisko et al. | |
| 7,242,923 B2 | 7/2007 | Perera et al. | |
| 7,290,067 B2 | 10/2007 | Fukunaga et al. | |
| 7,305,511 B2 | 12/2007 | Barrett et al. | |
| 7,400,891 B2 | 7/2008 | Aaron | |
| 7,408,438 B2 | 8/2008 | Izumi | |
| 7,475,245 B1 | 1/2009 | Healy et al. | |
| 7,486,048 B2 | 2/2009 | Tsukamoto et al. | |
| 7,518,502 B2 | 4/2009 | Austin et al. | |
| 7,562,167 B2 | 7/2009 | Anderson | |

(Continued)

OTHER PUBLICATIONS

International Search Report and Written Opinion received in PCT/US2010/054286 Jan. 19, 2011.

(Continued)

*Primary Examiner* — Allen Porter, Jr.
(74) *Attorney, Agent, or Firm* — Withers & Keys, LLC

(57) ABSTRACT

Devices and systems provide for proximity based selection of an implantable medical device for far field communication with an external device. By using a proximity communication that is limited to the IMD of interest during the selection process, the external device can eliminate those IMDs that are in range of far field communications but are able to receive the proximity communication. Thus, information may be shared via a proximity communication that is validated via a far field communication, or shared via a far field communication as a challenge and then validated via a proximity communication. The proximity communication may be used to initially limit the number of devices that respond to a discovery request and then subsequently used to select the intended implantable medical device as well as automatically select the appropriate therapy application corresponding to the selected IMD.

8 Claims, 8 Drawing Sheets

(56) References Cited

U.S. PATENT DOCUMENTS

| | | |
|---|---|---|
| 7,590,100 B2 | 9/2009 | Smith et al. |
| 7,623,922 B2 | 11/2009 | Bange et al. |
| 7,650,192 B2 | 1/2010 | Wahlstrand |
| 2003/0114897 A1 | 6/2003 | Von Arx |
| 2003/0119568 A1 | 6/2003 | Menard |
| 2004/0260363 A1* | 12/2004 | Arx et al. ............... 607/60 |
| 2005/0203582 A1 | 9/2005 | Healy |
| 2006/0020304 A1 | 1/2006 | Torgerson et al. |
| 2006/0252457 A1 | 11/2006 | Schrager |
| 2006/0287593 A1 | 12/2006 | Jaggu et al. |
| 2007/0118188 A1* | 5/2007 | Von Arx et al. ............... 607/60 |
| 2007/0129767 A1 | 6/2007 | Wahlstrand |
| 2008/0044014 A1 | 2/2008 | Corndorf |
| 2008/0044025 A1 | 2/2008 | Corndorf |
| 2008/0046039 A1 | 2/2008 | Corndorf |
| 2008/0140160 A1 | 6/2008 | Goetz et al. |
| 2009/0069868 A1 | 3/2009 | Bengtsson |
| 2009/0182426 A1 | 7/2009 | Von Arx |
| 2009/0248115 A1 | 10/2009 | Corndorf et al. |
| 2009/0252042 A1 | 10/2009 | Bradley et al. |
| 2009/0291656 A1 | 11/2009 | Le Reverend et al. |
| 2010/0179619 A1 | 7/2010 | Gray |
| 2011/0022123 A1 | 1/2011 | Stancer et al. |
| 2011/0054780 A1 | 3/2011 | Dhanani et al. |

OTHER PUBLICATIONS

U.S. Appl. No. 12/686,994, filed Jan. 13, 2010.
U.S. Appl. No. 12/686,994 Office Action dated Feb. 29, 2012.
U.S. Appl. No. 12/686,994 Response filed May 23, 2012.
U.S. Appl. No. 12/686,994 Notice of Allowance issued Jul. 20, 2012.

* cited by examiner

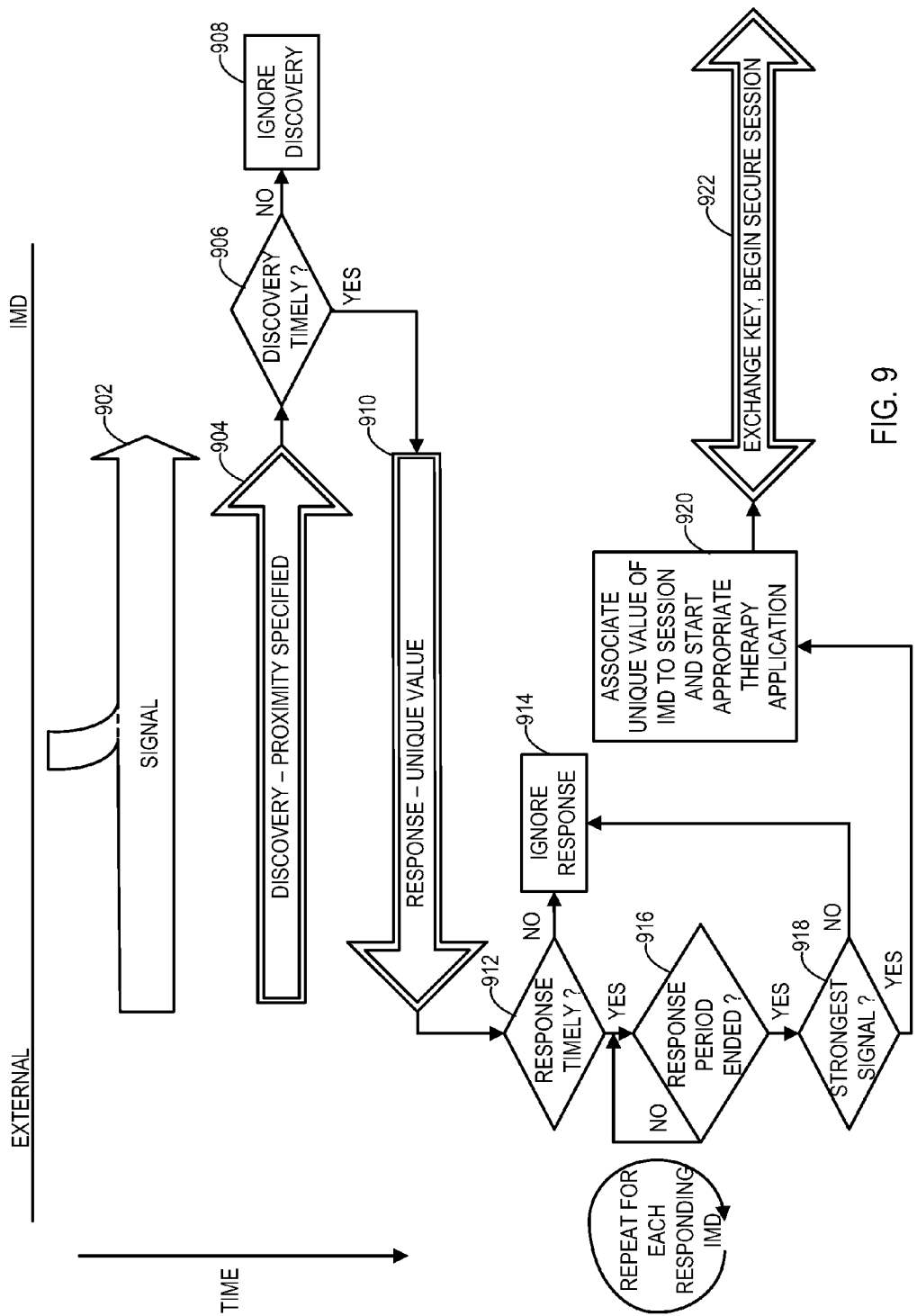

PROXIMITY BASED SELECTION OF AN IMPLANTABLE MEDICAL DEVICE FOR FAR FIELD COMMUNICATION

TECHNICAL FIELD

Embodiments relate to far field communications between external devices and implantable medical devices. More particularly, embodiments relate to the selection of an implantable medical device for far field communication with an external device on the basis of proximity.

BACKGROUND

Conventionally, external devices such as clinician and patient programmers communicate with an implantable medical device (IMD) through a near field form of communication such as an inductive coupling. Due to the short range of the inductive coupling, a telemetry head is placed in close proximity to the IMD to establish the inductive link. Because the telemetry head has a very short range and consequently is in such close proximity to the IMD, there is essentially no risk of inadvertently communicating with a different nearby IMD.

Far field communication has become an alternative to the use of near field links between external devices and implantable medical devices. Far field communication uses frequencies that allow for electromagnetic signal propagation over significantly larger distances than the maximum distance of near field links. This increased range of signals allows an external device to communicate with the IMD without placing a telemetry head in close proximity to the IMD. However, the increased range of the far field communication creates issues that are not a concern for near field links.

In particular, far field communication by the external device creates the possibility that other IMDs besides the intended IMD are in communication range of the external device. Therefore, the external device must either have advance knowledge of an identifier of the desired IMD or the external device must receive a user selection from a list of IMDs that respond to a discovery signal by the external device. Requiring the user to select the proper IMD from a list adds extra time and burden to the process and also presents an opportunity for human error where the user may select the wrong device and/or application for an intended device.

SUMMARY

Embodiments address issues such as these and others by providing devices, systems, and methods that utilize physical proximity of an external component relative to an intended IMD to allow the external device to select the intended IMD for a far field communication session and ultimately eliminate pairing between external devices and unintended IMDs within range of far field communications. One or more various forms of proximity communication occur between the external device and the IMD during the establishment of the far field communication session. The various forms of proximity communication occur within a short distance from the IMD so that the proximity communication intentionally does not extend to any unintended IMDs that may be nearby. In some cases, the physical proximity may be removed once the far field communication has been appropriately confirmed through the proximity communication. The pairing of the intended IMD with the external device may in some cases then allow for additional benefits such as the ability of the external device to automatically run the correct application for the intended IMD.

A form of proximity communication may share unique information between the external device and the IMD that can then be verified using a far field communication. This allows the external device to confirm that the IMD is the intended one while unintended IMDs do not have access to the unique information and cannot verify the unique information through far field communication with the external device which allows the external device to filter out discovery responses from the unintended IMDs. A form of proximity communication may trigger the IMD to respond to a far field discovery request by the external device while unintended IMDs that do not receive a proximity communication at that time would not respond to the far field discovery request. A form of proximity communication may be used by one device to satisfy a challenge issued over a far field communication by the other device to confirm that the far field communication is between the devices that are in physical proximity to one another.

DESCRIPTION OF THE DRAWINGS

FIG. 9 shows a sixth example of a procedure to establish a far field communication session where the external device considers far field signal strength when selecting the IMD for the far field communication session.

DETAILED DESCRIPTION

Embodiments provide for devices, systems, and methods that allow an external device to select an IMD for far field communication by using a proximity communication that is limited to the IMD of interest. In doing so, the external can eliminate those IMDs that are in range of far field communications but are not privy to the proximity communication.

Figure 1:
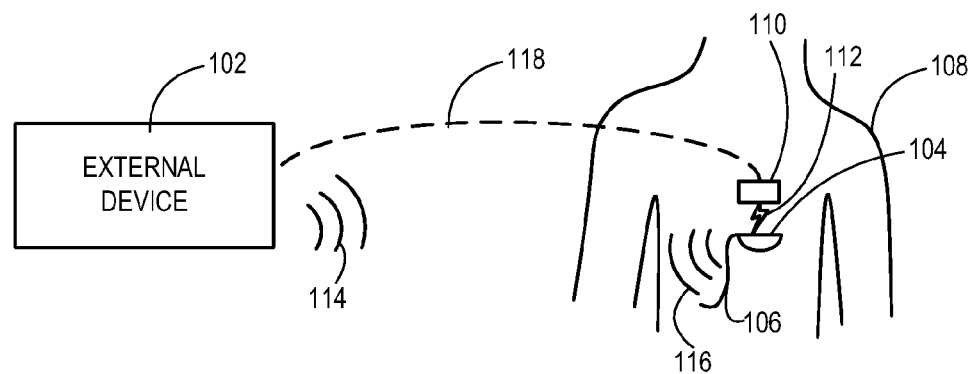
FIG. 1 shows a typical operating environment for embodiments where an external device and an IMD utilize proximity communication to establish a far field communication session.

FIG. 1 shows an environment that includes an external device 102, such as a clinician programmer, patient programmer, or a remote/home monitoring device that is nearby a patient 108 who has an IMD 104. The IMD 104 may be implanted within or mounted externally to the body 108 and may perform one or more medical tasks such as cardiac or neurological stimulation, physiological sensing, drug infusion, and the like. The IMD 104 may include components 106 such as stimulation or sensing leads or drug delivery catheters that extend from the IMD 104 and terminate at the target area of the body 108.

The external device 102 ultimately communicates with the IMD 108 through a far field communication session utilizing far field signals 114 sent by the external device 102 and far field signals 116 sent by the IMD 108. These far field signals 114, 116 may be radio frequency (RF) signals such as those of the Medical Implant Communications Service (MICS) band, the Industrial, Scientific, and Medical (ISM) band, or the short range device (SRD) band. The far field communication session may be used to program a medical therapy to the IMD, to obtain information from the IMD regarding therapy and patient information, and the like.

While the single IMD 104 is shown in FIG. 1, it will be appreciated that there may be other IMDs and/or other external devices nearby and in range of the far field signals 114 of the external device 102. The external device 102 may not be aware of identification information of the intended IMD 104 in advance such that the external device 102 cannot immediately discern far field communications of the intended IMD 104 relative to far field communications of other IMDs. However, physical proximity can be established to allow proximity communication to occur between the external device 102 and the intended IMD 104. Therefore, a procedure is provided that utilizes this physical proximity at the initiation of the far field communication session to avoid the external device 102 conducting a far field communication session with an unintended nearby IMD. To allow the external device 102 to select the intended IMD 104 for far field communication and avoid selecting an unintended nearby IMD, proximity communication signals 112 may be exchanged between a proximity communicator 110 and the IMD 104 during the establishment of the far field communication session.

The proximity communicator 110 may be of various forms and may be a separate component of the external device 102 or be integrated with the external device 102, or a combination of both. For instance, the proximity communicator 110 may be a near field telemetry head that is tethered to the external device 102 by a communication path 118 such as a cable or wireless connection and that establishes an inductive link with the IMD 104. As another example, the proximity communicator 110 may be an audible tone generator where the IMD 104 receives and recognizes different audible tones. As another example, the proximity communicator 110 may be a body thump device, such as a chest thump device, where the IMD 104 detects the thump through an on-board accelerometer or other vibration detector. As yet another example, the proximity communicator 110 may be a static field generating device such as an electromagnet or a permanent magnet being moved into and out of proximity with the IMD 104 by the clinician.

In some cases including the near field telemetry head, the audible signal generator, the body thump device, and the electromagnet, the proximity communicator 110 may be under control of the external device 102 through a tethered or wireless connection between the telemetry head 110 and the external device 102. In some cases including the clinician providing the body thump or moving the permanent magnet, the proximity communicator 110 is under direct control of the clinician who may be following commands being issued by the external device 102 to provide or remove the proximity communication.

The proximity communication may range from being a simple present or absent signal to a more complex signal carrying data. Furthermore, the proximity communication may be a unidirectional communication mode in some embodiments, particularly where the communication is simple. This may reduce the cost and complexity of a device, particularly the IMD 104. The proximity communication may be a bi-directional communication mode in other embodiments, such as where one device may send data through a proximity communication while the other device may send an acknowledgement through a subsequent proximity communication. This may improve the efficiency of the proximity communication procedure.

Figure 2:
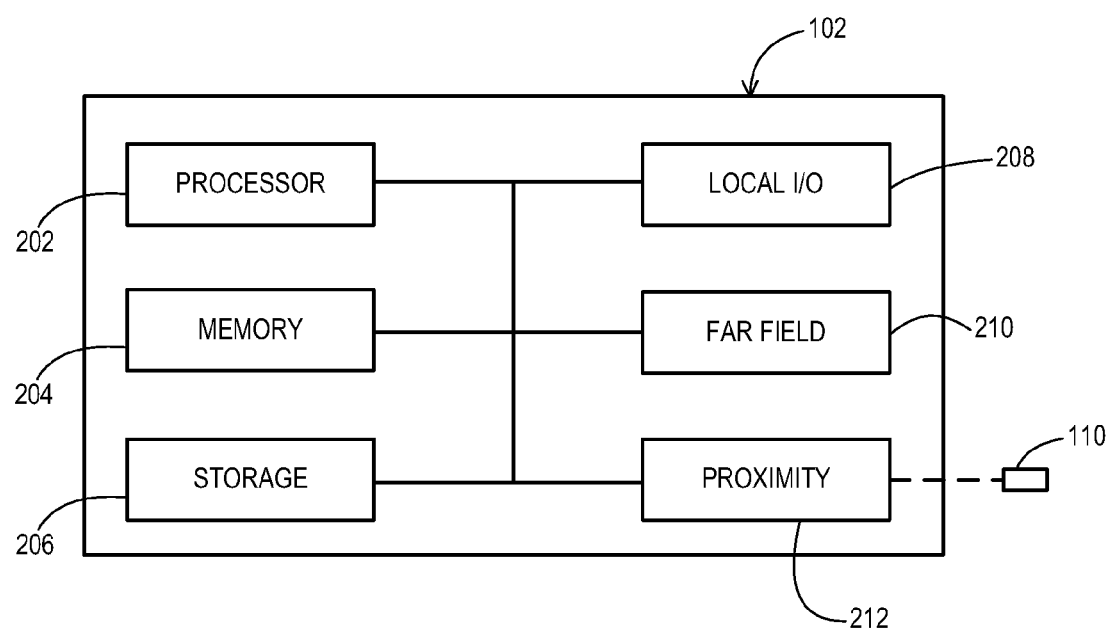
FIG. 2 shows components for one example of an external device embodiment.

FIG. 2 shows components of one example of the external device 102. The external device 102 includes a processor 202, a memory 204, and a storage device 206. The external device 102 may also include local input/output (I/O) ports 208 such as to provide local screen displays and to receive user input via keyboard, mouse, and so forth. The external device 102 also includes far field communication circuitry 210 used to establish the far field communication session with the IMD 104. The far field communication circuitry 210 may drive a signal propagation tool such as an RF antenna. The signal propagation tool may be included within the proximity communicator 110 so that the far field communication circuitry 210 instructs the signal propagation tool over the connection 118 or the signal propagation tool may be a separate external component or housed within the external device 102.

In addition to the far field communication circuitry 210, the external device 102 also includes proximity communication circuitry 212. The proximity communication circuitry 212 may be of various forms to interact with the proximity communicator 110. The link between the proximity communication circuitry 212 and the proximity communicator 110 may be a wired or wireless connection, for example using universal serial bus protocol, Bluetooth® protocol, or other such protocols, that provides data commands to circuitry within the proximity communicator 110 to produce the proximity communication signal. The proximity communicator 110 may then include a near field inductive driver circuit, a signal generator for producing audible tones, a motion signal generator for driving a body thump device, a field producing circuit for driving an electromagnet, and the like that are responsive to the data commands. Alternatively for a wired connection, these circuits may be included in the proximity communication circuitry 212 to drive the proximity communicator 110 directly.

The external device 102 may include additional communication capabilities that may be provided by far field communication circuitry 210 or by additional communication circuitry. For instance, the external device 102 may include Wi-Fi connectivity, public switched telephone network connectivity, and so forth to allow for remote communication, particularly where the external device 102 is a home/remote monitor.

The memory 204 may be used to store information in use by the processor 202. For instance, the memory 204 may store therapy parameters that are input by a clinician or patient that are to be loaded into the IMD 104. The memory 204 may also store programming that is used by the processor 202 to control the IMD selection procedure of the external device 102. The memory 204 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 202 that is implemented to control the IMD selection procedure. Examples of the storage device 206 include electronic, magnetic, and optical drives. The storage device 206 and the memory 204 are both examples of computer readable media that may store information in the form of computer programming, data structures, and the like.

The processor 202 performs logical operations to provide a sequence of far field and proximity communications and related decisions such as those of FIGS. 4-9 to allow far field communication sessions with the IMD 104 to be established. The processor 202 may be of various forms. For instance, the processor 202 may be a general-purpose programmable processor that executes software that is stored on the storage device 206 or elsewhere. Other examples include a dedicated purpose hardware circuit or hard-wired digital logic. The processor 202 may be multiple separate components or processors, dedicated hardware/state machine, and the like. The processor 202 may communicate with the various other components through one or more data buses.

Figure 3:
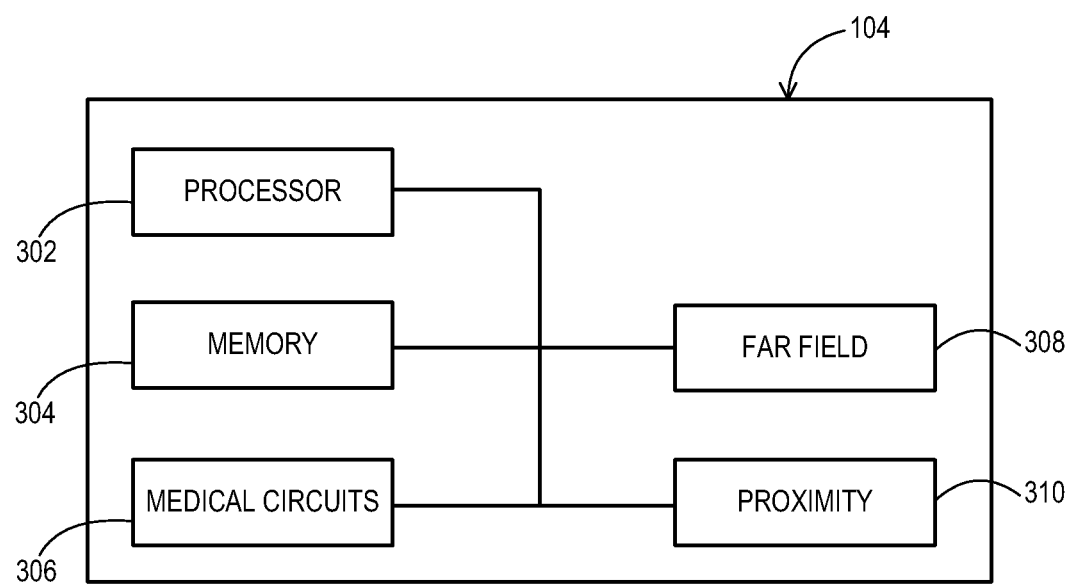
FIG. 3 shows components for one example of an IMD embodiment.

FIG. 3 shows components of one example of the IMD 104. The IMD 104 includes a processor 302 and a memory 304. The IMD 104 also includes medical circuitry 306 that performs a medical task such as stimulation, drug delivery, monitoring, and the like. The IMD 104 also includes far field communication circuitry 308 used to establish the far field communication session with the external device 102. The far field communication circuitry 308 may drive a signal propagation tool such as an integral RF antenna.

In addition to the far field communication circuitry 308, the IMD 104 also includes proximity communication circuitry 310. The proximity communication circuitry 310 may be of various forms where for a given system, the type of proximity communication circuitry 310 matches the type of proximity communicator 110 that the external device 102 includes. Accordingly, the proximity communication circuitry 310 may be a near field inductive receiver, a microphone for receiving audible tones, an accelerometer or other vibration detection device, a field operable switch such as a magnetic reed switch, and the like.

The memory 304 may be used to store information in use by the processor 302 such as programming and data values. The memory 304 may store additional information including therapy parameters that are used to control the medical circuitry 306. The memory 304 may be of various types such as volatile, non-volatile, or a combination of the two. The memory 304 is also an example of computer readable media that may store information in the form of computer programming, data structures, and the like.

The processor 302 performs logical operations to provide a sequence of far field and proximity communications and related decisions such as those of FIGS. 4-9 to allow far field communication sessions with the external device 102 to be established. The processor 302 may be of various forms like those discussed above for the processor 202 of the external device 102 and as discussed above may be multiple separate components or processors, dedicated hardware/state machine, and the like. The processor 302 may communicate with the various other components through one or more data buses.

FIGS. 4-9 describe proximity based communications. While these examples show proximity communications being directed from an external device 102 to an IMD 104, it will be appreciated that in some cases the roles may be reversed and the direction of the proximity communications may be reversed whereby the IMD 104 may send proximity communications rather than or in addition to the external device 102 doing so.

Figure 4:
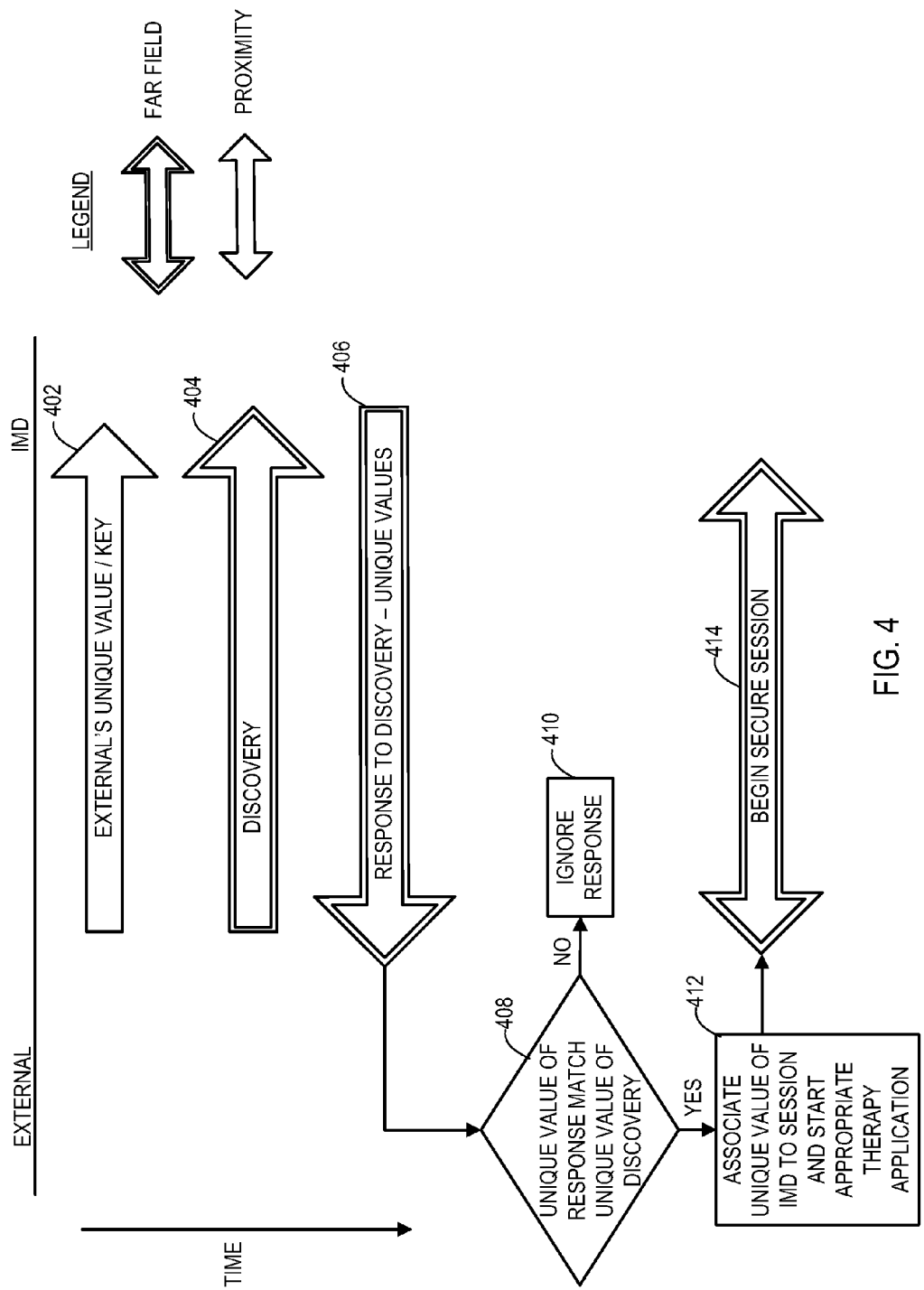
FIG. 4 shows a first example of a procedure to establish a far field communication session where a unique value and/or key are shared via a proximity communication.

FIG. 4 shows a first example of a procedure to establish a far field communication session where a unique value and/or key are shared via a proximity communication. The proximity communication is of a type that can carry data. Furthermore, the proximity communication may be bi-directional so that an acknowledgement may be returned as a confirmation of receipt of the data so that a successful initial data transfer via the proximity communication can be completed as a prerequisite to attempting subsequent steps.

Initially, the external device 102 may send a proximity communication 104 that includes a value that is unique to the external device 102 to the IMD 104. For example, the unique value may be a device serial number, hardware identification number, randomly generated number, a security key value, a combination, or other such values that may be unique to the external device 102. Because this information is transferred through the proximity communication 402, no other nearby IMD will receive this information. The external device 102 also sends a far field discovery communication 404 shortly before, during, or shortly after sending the proximity communication 402. The IMD 104 as well as other nearby IMDs may receive and respond to this far field discovery communication 404.

In one example, the IMD 102 may respond only to a discovery request that is within a certain time of receiving the proximity communication 402, such as a simultaneous occurrence of the proximity communication 402 and the discovery communication 404 or within a predefined delay from one to the next. In this example, the IMD 104 and potentially other nearby IMDs as well are configured to respond by sending the unique value that each has received via a proximity communication and also by sending a value that is unique to the IMD. For example, this value may be a device serial number, hardware identification number, randomly generated number, a security key value, a combination, or other such values that may be unique to the IMD 104.

Only the far field response communication 406 from the IMD 104 of interest will have the unique value that corresponds to the external device 102. Other IMDs would either have no unique value of an external device to send or would send the unique value of a different external device. Furthermore, in some examples, only those IMDs that receive the discovery communication 404 within a specified time relative to a proximity communication, such as the proximity communication 402 received by the intended IMD 104, bother to respond with a far field response communication such as the far field response communication 406 from the intended IMD 104.

For each far field response communication, the external device 102 attempts to verify the shared unique value by determining whether the unique value being received matches the unique value that was previously sent over the proximity communication 402 at a query operation 408. If a particular response does not include a matching value, then that particular response is ignored at operation 410. For the response 406 which does have the matching unique value from the proximity communication 402, the external device 102 then associates the value that is unique to the IMD 104 and that is included in the far field response communication 406 to the far field communication session being established at an association operation 412. The external device 102 may also then execute the appropriate therapy program automatically based on the value that is unique to the IMD 104 where the external device 102 stores associations of such values to therapy applications.

The external device 102 then begins the session with the IMD 104. The external device may communicate during the session by using the unique value of the external device 102 of which the IMD 104 is aware to identify the sender of transmissions and/or using the unique value of the IMD 104 to identify the intended recipient of transmissions. Likewise, the IMD may communicate during the session by using the unique value of the IMD 104 of which the external device 102 is aware to identify the sender of transmissions and/or using the unique value of the external device 102 to identify the intended recipient of transmissions.

The session may be made secure by encrypting the information with an encryption key. This encryption key may have been generated for the session by the external device 102 and included in the proximity communication 402 so that the IMD 104 already has the key. Alternatively, the key may be exchanged in another manner and/or at another time in the sequence such as by using a low power radio frequency communication to minimize the range. Furthermore, the IMD 104 may provide the key for the secure session rather than receiving the key from the external device 102.

In some cases, such as for an external device 102 that is a patient programmer or home monitoring device, the external device 102 and the IMD 104 may be bonded whereby each device is aware of an identification value of the other that is used to address far field communications and already possesses the encryption key used to secure the far field communications. In that case, the proximity based initiation of the far field communication session by a process like that of FIG. 4, as well as FIGS. 5-9 discussed below, may still be useful for various reasons. For instance, the initial proximity communication such as the proximity communication 402 may be used as a wake up signal for the far field communication circuits of the IMD 104. Additionally, to ensure that the use of the external device 102 to initiate the communication session is legitimate, as opposed to being an accident or a malicious attempt, proximity must be established before the far field communication session can begin. However, in such a case, the far field communication session can begin pursuant to the processes of FIGS. 4-9 but with omission of the discovery operations because the identification of the IMD 104 is known to the external device 102 so that it can immediately address an initial far field communication to the IMD 104.

For embodiments using processes such as those of FIGS. 4-9 where discovery via far field communications is attempted, the external device 102 and IMDs may be configured to apply collision avoidance and backoff algorithms. These algorithms allow devices to re-attempt to send and/or receive expected far field communications where two devices may attempt to send a far field communication at the same time such that neither transmission is received and acknowledged. A re-attempt to send the far field communication occurs by each of the sending devices but at different times on the second attempts because the backoff algorithm of each sending device randomly chooses the time for the re-attempt. This reduces the likelihood of collisions occurring multiple times.

Figure 5:
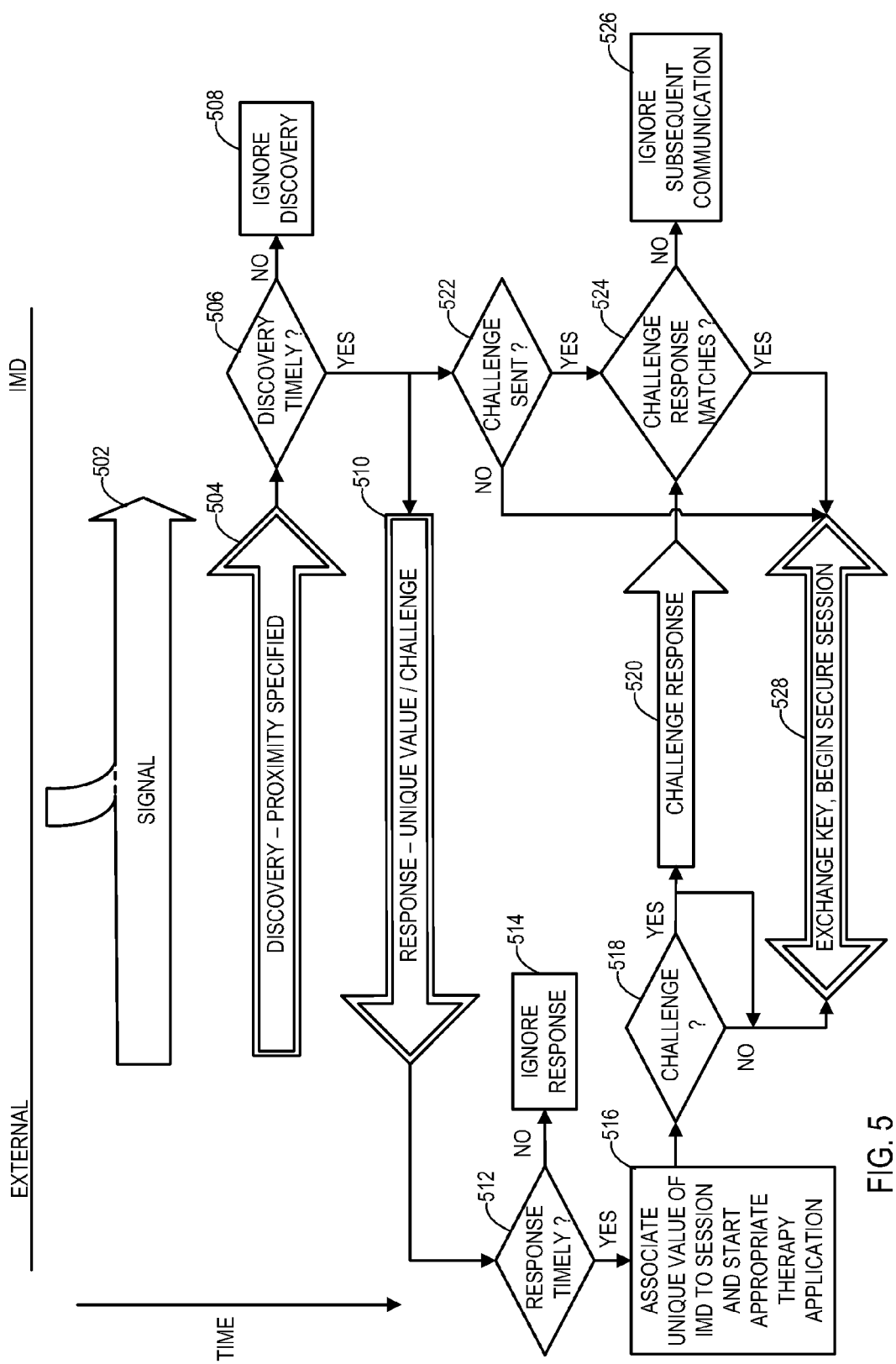
FIG. 5 shows a second example of a procedure to establish a far field communication session where a challenge is issued by the IMD during a discovery phase.

FIG. 5 shows a second example of a procedure to establish a far field communication session. In this particular example and as further discussed below, a challenge may be issued by the IMD during a discovery phase to provide confirmation that the correct IMD has been selected. Other examples of providing confirmation or otherwise selecting the appropriate IMD are discussed with reference to FIGS. 6-9.

Initially, the external device 102 provides a proximity communication 502 in the form of a signal. As discussed above, the proximity communication 502 may be provided by a third party such as the clinician acting at the request of the external device 102 such as to pass a magnet nearby the IMD 104 to provide a form of the proximity communication 502. In either case, this signal may be simple in terms of carrying no data but merely being on or off. Alternatively, this signal of the proximity communication 502 from the external device 102 may be more sophisticated including the ability to carry data such as communication identifiers, encryption key data, challenge data, and so forth. In either case, the IMD 104 may or may not have the ability to send a return proximity communication.

The proximity communication of these embodiments of FIGS. 4-9, such as the proximity communication 502 from the external device 102 may serve one or more purposes. For instance, the proximity communication 502 may serve as a trigger for the IMD 104 to respond to far field communication. Likewise, the proximity communication 502 may serve as a wake-up signal to the far field communication abilities of the IMD 104. This may be useful where the IMD 104 deactivates the far field communication abilities during periods of non-use and reactivates those abilities upon receiving a proximity communication 502. The opposite may also be true, where the IMD 104 uses the far field communication abilities to monitor for a far field wake up signal that then wakes up the proximity communication abilities of the IMD 104. In that case, the external device 102 may send a far field communication in advance of providing the proximity communication.

The external device 102 also sends a far field discovery communication 504. This far field discovery communication 504 may occur at some point shortly after the proximity communication 502, particularly in examples where the proximity communication 502 serves as a wake-up signal to the far field communication abilities of the IMD 104. The far field discovery communication 504 may occur shortly before or during the proximity communication 502, particularly in examples where the far field communication abilities of the IMD 104 are already functioning prior to the proximity communication 502.

The far field discovery communication 504 serves as an inquiry to all IMDs within range and triggers the receiving IMDs to provide a response that identifies the IMD such as by including a value unique to the IMD 104 in the response to the discovery. In one example, the far field discovery communication 504 specifies a condition for responding. The condition may be that the IMD responds only if the IMD is receiving the far field discovery communication 504 within a predefined time relative to receiving the proximity communication. In one example, the predefined time may be zero, such that the IMD must receive the proximity communication 502 at the time the far field discovery communication 504 is received in order to provide a response.

This condition may be specified by setting a bit value within the discovery request, where the predefined time is preconfigured within the logic of the IMD 104. This condition may alternatively be specified in a more complex manner such as by indicating the predefined amount of time within the request.

In another example, the criteria for responding are preconfigured within the IMD 104. So, in this case, the far field discovery communication 504 may omit any conditions, and the external device 102 may rely on the IMDs that receive the far field discovery communication 504 to properly determine whether to respond based upon the preconfiguration.

In this example, the IMD 104 detects whether the far field discovery communication has arrived within the predefined amount of time relative to receiving the proximity communication 502 at a query operation 506. For those IMDs where no proximity communication 502 has been received or has been received such that the far field discovery communication 504 is outside of the allowed window of time, the far field discovery communication 504 is ignored at an operation 508. For the intended IMD 104, the proximity communication 502 is received and the far field discovery communication arrives within the predefined time relative to the proximity communication 502 so that a far field response communication 510 is returned.

The far field response communication 510 may specify the value that is unique to the IMD 104. The external device 102 may then utilize this unique value to establish a communication session with the IMD 104. However, there is the possibility that multiple IMDs provide a response, including the intended IMD 104 as well as the other nearby IMDs who may have also had a proximity signal from other external devices present at the appropriate time relative to the far field discovery communication 504 from the external device 102. In that case, the external device 102 may not determine which IMD 104 is the correct one from the far field responses alone. The external device 102 may instead rely on a challenge procedure in order to ultimately confirm that the intended IMD 104 is the one that the external device 102 is communicating with via far field communications.

In this example, the challenge procedure may be provided by each IMD that is responding including a challenge within the far field response communication 510. The challenge may specify that the external device 102 provide a proximity communication that includes a challenge response. The challenge response may be of various types and may depend upon the type of proximity communication that is in use. For instance, where the proximity communication is a simple on or off state of a signal, the challenge may be to provide an on-off sequence, or to be on at only a certain time or for only a certain duration. As another example, where the proximity communication is capable of providing data, the challenge may be to repeat a particular data value or sequence.

In this example, the external device 102 may respond to receiving several responses by choosing one of the responses and attempting to satisfy the challenge. The choice may be based on time the response was received, strength of the response signal, a random selection, and the like. When choosing whether to respond to any one of the received responses, the external device 102 may detect whether each response is timely at a query operation 512 and ignore the response at an operation 514 if not.

The external device 102 may proceed to setup the communication session along with responding to the challenge for the chosen response. Initially, for the chosen response, the external device 102 may proceed to associate the unique value of the IMD received in the response to the session at an association operation 516. The external device 102 may also then execute the appropriate therapy program automatically based on the value that is unique to the IMD where the external device 102 stores associations of such values to therapy applications.

The external device 102 then determines that the challenge response is necessary at a query operation 518. A proximity communication 520 that provides the response to the challenge is sent if requested, and then the external device 102 attempts to begin a communication session with the selected IMD via an exchange of far field communications 528. In embodiments where no challenge was requested, such as where the external device 102 is using some other technique for selecting the correct IMD that has responded, then the external device may proceed with the far field communications 528 without sending the challenge response 520.

The IMD 104, upon sending the far field response communication 510 may then detect that a challenge has been sent at a query operation 522. For embodiments where no challenge is performed such as where the external device 102 uses some other technique for selecting the correct IMD 104 that has responded, then the IMD 104 may proceed with the far field communications 528 to establish the communication session whereby the IMD 104 responds to far field communications that include the unique value of the IMD 104 as the recipient.

For embodiments where the IMD 104 has issued the challenge to the external device 102, the IMD 104 may then detect whether the shared challenge is verified by detecting whether the challenge response has been received and whether the challenge response matches the challenge that was issued at a query operation 524. Because the IMD 104 is receiving proximity communications from the external device 102, the IMD 104 will receive the proximity communication 520 that includes the challenge response regardless of whether the external device 102 is responding to the challenge by the IMD 104 or a challenge by another nearby IMD. However, if the external device 102 is responding to a challenge by another nearby IMD, then because the challenge from each IMD is different the challenge response being provided to the IMD 104 will not match the challenge that was issued by the IMD 104. Accordingly, the IMD 104 will ignore all subsequent communication at an operation 526 because the external device 102 has selected another nearby and unintended IMD rather than the intended IMD 104. The IMD 104 may continue to ignore subsequent communication until the discovery process of FIG. 5 re-starts with another proximity communication 502 and far field discovery communication 504.

The other nearby IMD that has been incorrectly selected by the external device 102 will not receive the proximity communication 520 from the external device 102 that includes the challenge response because the other nearby IMD is not within range of the proximity communication 520. If this other IMD does not receive a challenge response, then this other nearby IMD also ignores all subsequent communication until the discovery process of FIG. 5 re-starts with another proximity communication 502 and far field discovery communication 504. However, the external device that is providing the proximity communication to this other IMD may have properly selected this other IMD and may provide a proximity communication that does satisfy the challenge of this other IMD so that a proper communication session may be established between them.

In the event the external device 102 has not adequately responded to the challenge, the external device 102 will need to re-attempt to discover, select, and establish a session with the intended IMD 104. However, where the external device 102 has selected the IMD 104 from the set of far field responses and responds by providing the proximity communication 520 that does satisfy the challenge by the intended IMD 104, then the external device 102 and the IMD 104 will both begin the far field communication session via subsequent far field communications 528.

The external device may communicate during the session by using the unique value of the external device 102 of which the IMD 104 has been made aware via a far field communication to identify the sender of transmissions and/or using the unique value of the IMD 104 to identify the intended recipient of transmissions. Likewise, the IMD 104 may communicate during the session by using the unique value of the IMD 104 of which the external device 102 is aware to identify the sender of transmissions and/or using the unique value of the external device 102 to identify the intended recipient of transmissions.

As with the example of FIG. 4, the session may be made secure by encrypting the information with an encryption key. This encryption key may have been generated for the session by the external device 102 and included in a far field communication so that the IMD 104 obtains the key. As one example, the key may be exchanged by using a low power radio frequency communication to minimize the range. Furthermore, the IMD 104 may provide the key for the secure session rather than receiving the key from the external device 102. To the extent the devices have a capable manner of using more complex proximity communications, the key may be exchanged through proximity communication rather than through far field communication.

Figure 6:
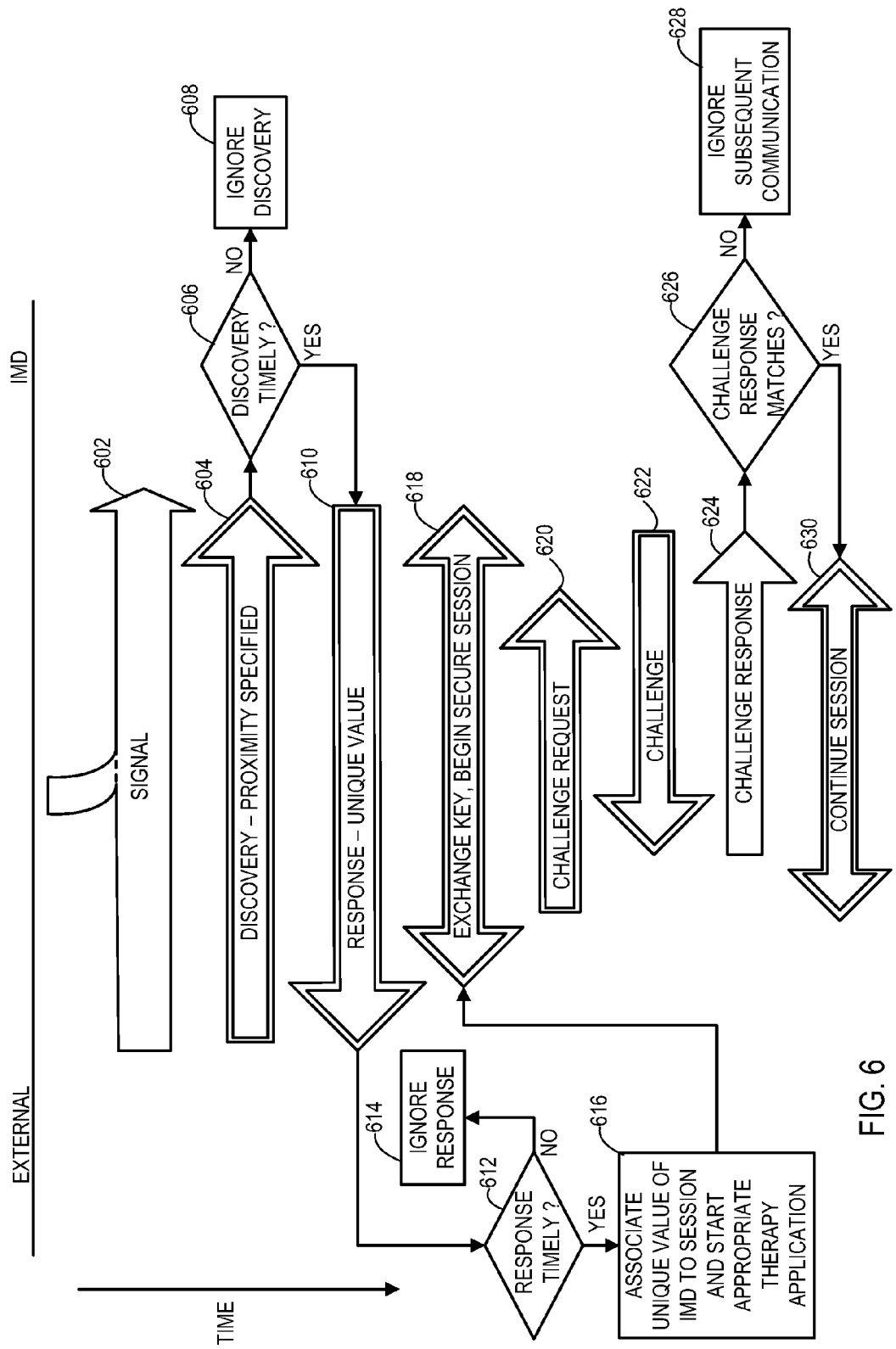
FIG. 6 shows a third example of a procedure to establish a far field communication session where the external device requests a challenge upon the far field communication session being established.

FIG. 6 shows a third example of a procedure to establish a far field communication session. In this particular example and as further discussed below, a challenge may be issued by the IMD upon the start of a far field communication session to provide confirmation that the correct IMD has been selected.

Initially, the external device 102 provides a proximity communication 602 in the form of a signal. As discussed above, the proximity communication 602 may be provided by a third party such as the clinician acting at the request of the external device 102 such as to pass a magnet nearby the IMD 104 to provide a form of the proximity communication 602. In either case, this signal may be simple in terms of carrying no data but merely being on or off. Alternatively, this signal of the proximity communication 602 from the external device 102 may be more sophisticated including the ability to carry data. In either case, the IMD 104 may or may not have the ability to send a return proximity communication.

As with FIG. 5, the proximity communication 602 from the external device 102 may serve one or more purposes. For instance, the proximity communication 602 may serve as a trigger for the IMD 104 to respond to far field communication. Likewise, the proximity communication 602 may serve as a wake-up signal to the far field communication abilities of the IMD 104.

The external device 102 also sends a far field discovery communication 604. This far field discovery communication 604 may occur at some point shortly after the proximity communication 602, particularly in examples where the proximity communication 602 serves as a wake-up signal to the far field communication abilities of the IMD 104. The far field discovery communication 604 may occur shortly before or during the proximity communication 602, particularly in examples where the far field communication abilities of the IMD 104 are already functioning prior to the proximity communication 602.

The far field discovery communication 604 serves as an inquiry to all IMDs within range and triggers the receiving IMDs to provide a response that identifies the IMD such as by including a value unique to the IMD 104 in the response to the discovery. In one example, the far field discovery communication 604 specifies a condition for responding. The condition may be that the IMD responds only if the IMD is receiving the far field discovery communication 604 within a predefined time relative to receiving the proximity communication. In one example, the predefined time may be zero, such that the IMD must receive the proximity communication 602 at the time the far field discovery communication 604 is received in order to provide a response.

This condition may be specified by setting a bit value within the discovery request, where the predefined time is preconfigured within the logic of the IMD 104. This condition may alternatively be specified in a more complex manner such as by indicating the predefined amount of time within the request.

In another example, the criteria for responding are preconfigured within the IMD 104. So, in this case, the far field discovery communication 604 may omit any conditions, and the external device 102 may rely on the IMDs that receive the far field discovery communication 604 to properly determine whether to respond based upon the preconfiguration.

In this example, the IMD 104 detects whether the far field discovery communication has arrived within the predefined amount of time relative to receiving the proximity communication 602 at a query operation 606. For those IMDs where no proximity communication 602 has been received or has been received such that the far field discovery communication 604 is outside of the allowed window of time, the far field discovery communication 604 is ignored at an operation 608. For the intended IMD 104, the proximity communication 602 is received and the far field discovery communication arrives within the predefined time relative to the proximity communication 602 so that a far field response communication 610 is returned.

The far field response communication 610 may specify the value that is unique to the IMD 104. The external device 102 may then utilize this unique value to establish a communication session with the IMD 104. However, there is the possibility that multiple IMDs provide a response in this example as well. These responding devices may include the intended IMD 104 as well as the other nearby IMDs who may have also had a proximity signal from other external devices present at the appropriate time relative to the far field discovery communication 604 from the external device 102. In that case, the external device 102 may not determine which IMD 104 is the correct one from the far field responses alone. The external device 102 may instead rely on another challenge procedure in order to ultimately confirm that the intended IMD 104 is the one that the external device 102 is communicating with via far field communications.

In this example, the challenge procedure may be provided by the external device 102 entering into a communication session with a selected one of the responding IMDs. The choice of IMD may be based on time the response was received, strength of the response signal, a random selection, and the like. The external device 102 then attempts to satisfy the challenge and then proceeds with the session if the challenge is satisfied or terminates the current session due to a failed challenge. If a challenge is failed, the external device 102 then starts a session with the next selected responding IMD to attempt to satisfy that challenge and this process continues until a challenge for a responding IMD is satisfied. As an alternative, the challenge procedure may be provided by the external device 102 entering into separate and simultaneous communication sessions with all of the responding IMDs. The external device 102 then attempts to satisfy the challenge of each one in sequence where sessions with failed challenges terminate and the session with the satisfied challenge proceeds.

When choosing whether to respond to any one of the received responses by establishing a communication session, the external device 102 may detect whether each response is timely at a query operation 612 and ignore the response at an operation 614 if not. The external device 102 may then proceed to setup the far field communication session(s) for the chosen response or alternatively for each of the responses.

The external device 102 may proceed to associate the unique value of the IMD received in the response to a given far field communication session at an association operation 616 and being far field communications 618. The external device 102 may also then execute the appropriate therapy program automatically based on the value that is unique to the IMD where the external device 102 stores associations of such values to therapy applications.

The external device 102 may communicate during the session by using the unique value of the external device 102 of which the IMD of the session has been made aware via a far field communication to identify the sender of transmissions and/or using the unique value of the IMD of the session to identify the intended recipient of transmissions. Likewise, the IMD of the session may communicate during the session by using the unique value of the IMD of the session of which the external device 102 is aware to identify the sender of transmissions and/or using the unique value of the external device 102 to identify the intended recipient of transmissions.

As with the example of FIG. 4, each session may be made secure by encrypting the information with an encryption key, where each session may utilize a different key. This encryption key may have been generated for the session by the external device 102 and included in a far field communication so that the IMD of the session obtains the key. Furthermore, the IMD 104 may provide the key for the secure session rather than receiving the key from the external device 102.

Upon starting the communication session, the external device 102 of this particular example then sends a far field communication 620 that includes a challenge request that is addressed with the unique value of the IMD of the session. The challenge request triggers the IMD of the session to return a challenge and to monitor for a challenge response via a proximity communication. In some embodiments, the IMD may detect whether the proximity challenge is timely and if not, then ignore subsequent far field communications from the external device 102.

When appropriate, the IMD of each of the sessions sends the far field communication 622 that may include the unique value of the external device 102 and includes the challenge. The challenge may specify that the external device 102 provide a proximity communication that includes a challenge response. As discussed above for the example in FIG. 5, the challenge response may be of various types and may depend upon the type of proximity communication that is in use. For instance, where the proximity communication is a simple on or off state of a signal, the challenge may be to provide an on-off sequence, or to be on at only a certain time or for only a certain duration. As another example, where the proximity communication is capable of providing data, the challenge may be to repeat a particular data value or sequence.

The external device 102 then sends a proximity communication 624 for the session or sessions that provides the response to the challenge. The proximity communication 624 may also be addressed with the unique value of the IMD of the session. Then the external device 102 attempts to continue the communication session with the IMD of the session via an exchange of subsequent far field communications 630.

The IMD of the session detects whether the shared challenge is verified by detecting whether the challenge response has been received and matches the challenge that was issued at a query operation 626. Because the IMD 104 is receiving proximity communications from the external device 102, the IMD 104 will receive the proximity communication 624 that includes the challenge response regardless of whether the external device 102 is responding to the challenge by the IMD 104 or a challenge by another nearby IMD. In the situation where the IMD 104 has yet to issue the challenge either because the external device 102 has yet to establish the communication session with the IMD 104 or because it is not yet the turn of the IMD 104 to receive a challenge request, then the IMD 104 may simply ignore the proximity communication 624.

In that case, the proximity communication that includes the challenge response is a result of the external device 102 responding to a challenge by another nearby IMD. This other nearby IMD that has been incorrectly selected by the external device 102 will not receive the proximity communication 624 that includes the challenge response because this other nearby IMD is not within range of the proximity communication 624. Thus, this other nearby IMD will detect that a matching response has not been received at a query operation 626. As a result, the other nearby IMD also ignores all subsequent communication at an operation 628 until the discovery process of FIG. 6 re-starts with another proximity communication 602 and far field discovery communication 604.

In the event the external device 102 has not adequately responded to the challenge, the external device 102 will need to re-attempt to discover, select, and establish a session with the intended IMD 104. However, where the external device 102 has selected the IMD 104 from the set of far field responses and responds by providing the proximity communication 624 that does satisfy the challenge by the intended IMD 104 at the query operation 626, then the external device 102 and the IMD 104 will both continue the far field communication session via subsequent far field communications 630. The external device 102 may then cease attempting to satisfy any remaining challenges of other responding IMDs, and those IMDs ignore subsequent communications until the discovery process of FIG. 6 re-starts.

Figure 7:
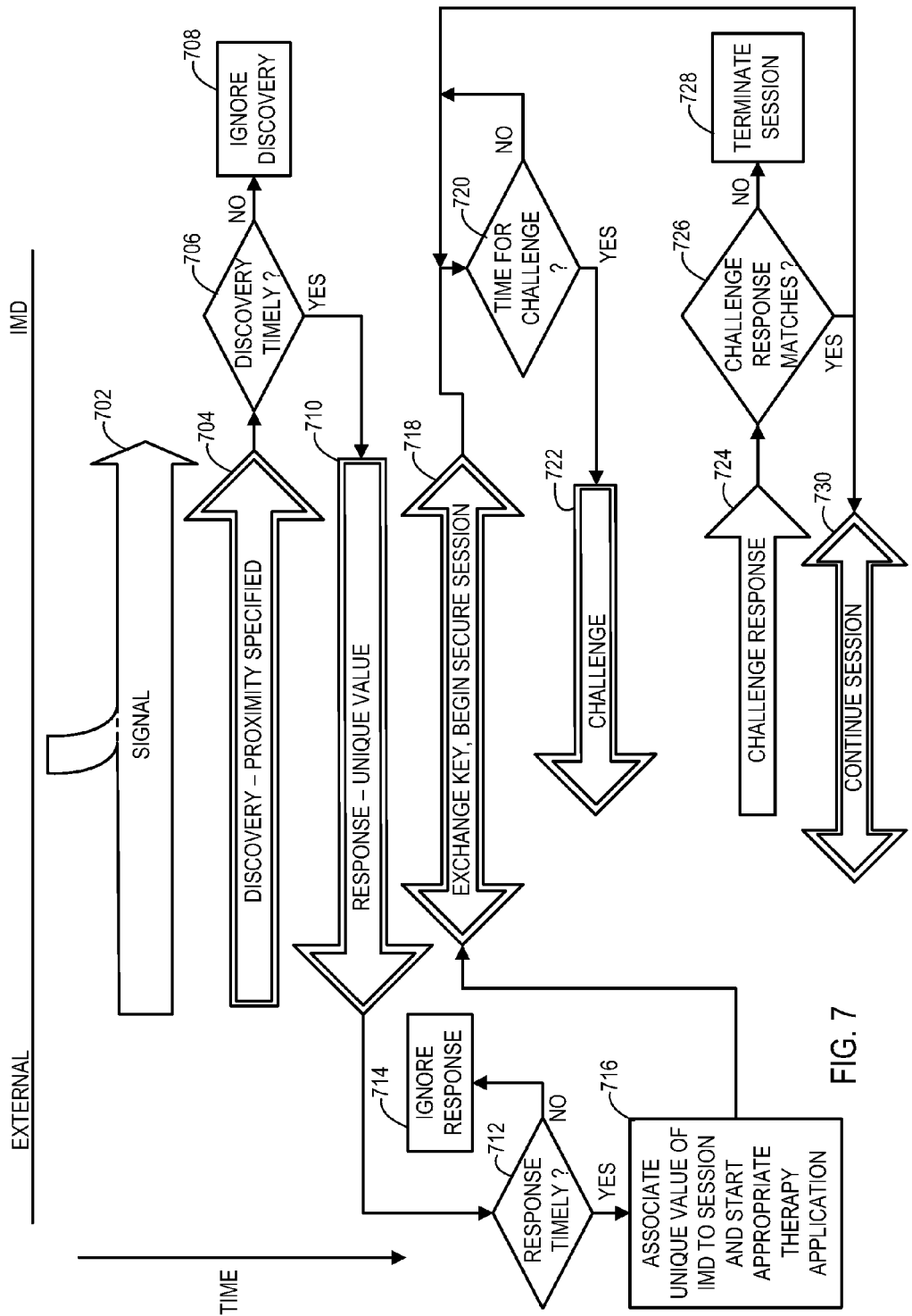
FIG. 7 shows a fourth example of a procedure to establish a far field communication session where the IMD issues a challenge upon the far field communication session being established.

FIG. 7 shows a fourth example of a procedure to establish a far field communication session. In this particular example and as further discussed below, a challenge may be issued by the IMD 104 at the onset of the far field communication session to provide confirmation that the correct IMD has been selected. Additionally or alternatively, the IMD 104 may issue the challenge at one or more subsequent times during the communication session which allows the IMD 104 to periodically confirm that far field communications are with the intended external device 102.

Initially, the external device 102 provides a proximity communication 702 in the form of a signal. As discussed above, the proximity communication 702 may be provided by a third party such as the clinician acting at the request of the external device 102 such as to pass a magnet nearby the IMD 104 to provide a form of the proximity communication 702. In either case, this signal may be simple in terms of carrying no data but merely being on or off. Alternatively, this signal of the proximity communication 702 from the external device 102 may be more sophisticated including the ability to carry data. In either case, the IMD 104 may or may not have the ability to send a return proximity communication.

As with FIG. 5, the proximity communication 702 from the external device 102 may serve one or more purposes. For instance, the proximity communication 702 may serve as a trigger for the IMD 104 to respond to far field communication. Likewise, the proximity communication 702 may serve as a wake-up signal to the far field communication abilities of the IMD 104.

The external device 102 also sends a far field discovery communication 704. This far field discovery communication 704 may occur at some point shortly after the proximity communication 702, particularly in examples where the proximity communication 702 serves as a wake-up signal to the far field communication abilities of the IMD 104. The far field discovery communication 704 may occur shortly before or during the proximity communication 702, particularly in examples where the far field communication abilities of the IMD 104 are already functioning prior to the proximity communication 702.

The far field discovery communication 704 serves as an inquiry to all IMDs within range and triggers the receiving IMDs to provide a response that identifies the IMD such as by including a value unique to the IMD 104 in the response to the discovery. In one example, the far field discovery communication 704 specifies a condition for responding. The condition may be that the IMD responds only if the IMD is receiving the far field discovery communication 704 within a predefined time relative to receiving the proximity communication. In one example, the predefined time may be zero, such that the IMD must receive the proximity communication 702 at the time the far field discovery communication 704 is received in order to provide a response.

This condition may be specified by setting a bit value within the discovery request, where the predefined time is preconfigured within the logic of the IMD 104. This condition may alternatively be specified in a more complex manner such as by indicating the predefined amount of time within the request.

In another example, the criteria for responding are preconfigured within the IMD 104. So, in this case, the far field discovery communication 704 may omit any conditions, and the external device 102 may rely on the IMDs that receive the far field discovery communication 704 to properly determine whether to respond based upon the preconfiguration.

In this example, the IMD 104 detects whether the far field discovery communication has arrived within the predefined amount of time relative to receiving the proximity communication 702 at a query operation 706. For those IMDs where no proximity communication 702 has been received or has been received such that the far field discovery communication 704 is outside of the allowed window of time, the far field discovery communication 704 is ignored at an operation 708. For the intended IMD 104, the proximity communication 702 is received and the far field discovery communication arrives within the predefined time relative to the proximity communication 702 so that a far field response communication 710 is returned.

The far field response communication 710 may specify the value that is unique to the IMD 104. The external device 102 may then utilize this unique value to establish a communication session with the IMD 104. However, there is the possibility that multiple IMDs provide a response in this example as well. These responding devices may include the intended IMD 104 as well as the other nearby IMDs who may have also had a proximity signal from other external devices present at the appropriate time relative to the far field discovery communication 704 from the external device 102. In that case, the external device 102 may not determine which IMD 104 is the correct one from the far field responses alone. The external device 102 may instead rely on another challenge procedure in order to ultimately confirm that the intended IMD 104 is the one that the external device 102 is communicating with via far field communications.

In this example, the challenge procedure may be provided by the external device 102 entering into a communication session with a selected one of the responding IMDs. The choice of IMD may be based on time the response was received, strength of the response signal, a random selection, and the like. The external device 102 then attempts to satisfy the challenge and then proceeds with the session if the challenge is satisfied or terminates the current session due to a failed challenge. If a challenge is failed, the external device 102 then starts a session with the next selected responding IMD to attempt to satisfy that challenge and this process continues until a challenge for a responding IMD is satisfied. As an alternative, the challenge procedure may be provided by the external device 102 entering into separate and simultaneous communication sessions with all of the responding IMDs. The external device 102 then attempts to satisfy the challenge of each one in sequence where sessions with failed challenges terminate and the session with the satisfied challenge proceeds.

When choosing whether to respond to any one of the received responses by establishing a communication session, the external device 102 may detect whether each response is timely at a query operation 712 and ignore the response at an operation 714 if not. The external device 102 may then proceed to setup the far field communication session(s) for the chosen response or alternatively for each of the responses.

The external device 102 may proceed to associate the unique value of the IMD received in the response to a given far field communication session at an association operation 716 and begin sending far field communications 718. The external device 102 may also then execute the appropriate therapy program automatically based on the value that is unique to the IMD where the external device 102 stores associations of such values to therapy applications.

The external device 102 may communicate during the session by using the unique value of the external device 102 of which the IMD of the session has been made aware via a far field communication to identify the sender of transmissions and/or using the unique value of the IMD of the session to identify the intended recipient of transmissions. Likewise, the IMD of the session may communicate during the session by using the unique value of the IMD of the session of which the external device 102 is aware to identify the sender of transmissions and/or using the unique value of the external device 102 to identify the intended recipient of transmissions.

As with the example of FIG. 4, each session may be made secure by encrypting the information with an encryption key, where each session may utilize a different key. This encryption key may have been generated for the session by the external device 102 and included in a far field communication so that the IMD of the session obtains the key. Furthermore, the IMD of the session may provide the key for the secure session rather than receiving the key from the external device 102.

Upon starting the communication session(s), the IMD of a session in this particular example begins detecting whether it is time to challenge the external device 102 at a query operation 720. For instance, the IMD of a session may be configured to challenge the IMD immediately upon the communication session being established. In this case, the IMD of a session may challenge the external device 102 to provide confirmation at the onset of the communication session without the external device 102 first having to request the challenge. Furthermore, the IMD of a session additionally or alternatively determines that such a challenge is necessary at some later time during the session so that confirmation throughout the session may occur. It will be appreciated that in some examples, the external device 102 may request one or more challenges, as in FIG. 6, while the IMD 104 may respond to those and may also generate one or more challenges to the external device 102 without receiving a request as in FIG. 7.

In the example of FIG. 7, the IMD of the session sends the far field communication 722 that includes the challenge. The challenge may specify that the external device 102 provide a proximity communication that includes a challenge response. As discussed above for the example in FIG. 5, the challenge response may be of various types and may depend upon the type of proximity communication that is in use. For instance, where the proximity communication is a simple on or off state of a signal, the challenge may be to provide an on-off sequence, or to be on at only a certain time or for only a certain duration. As another example, where the proximity communication is capable of providing data, the challenge may be to repeat a particular data value or sequence.

The external device 102 then sends a proximity communication 724 for the session that provides the response to the challenge. Then the external device 102 attempts to continue the communication session with the IMD of the session via an exchange of subsequent far field communications 730.

The IMD of the session detects whether the shared challenge is verified by detecting whether the challenge response has been received and matches the challenge that was issued at a query operation 726. Because the intended IMD 104 is receiving proximity communications from the external device 102, the intended IMD 104 will receive the proximity communication 724 that includes the challenge response regardless of whether the external device 102 is responding to the challenge by the IMD 104 or a challenge by another nearby IMD. In the situation where the IMD 104 has yet to issue the challenge because the external device 102 has yet to establish the communication session with the IMD 104, then the IMD 104 may simply ignore the proximity communication 724.

In that case, the proximity communication that includes the challenge response is a result of the external device 102 responding to a challenge by another nearby IMD. This other nearby IMD that has been incorrectly selected by the external device 102 will not receive the proximity communication 724 that includes the challenge response because this other nearby IMD is not within range of the proximity communication 724. Thus, this other nearby IMD will detect that a matching response has not been received at a query operation 726. As a result, the other nearby IMD also ignores all subsequent communication and terminates the session at an operation 728 until the discovery process of FIG. 7 re-starts with another proximity communication 702 and far field discovery communication 704.

In the event the external device 102 has not adequately responded to the challenge, the external device 102 will need to re-attempt to discover, select, and establish a session with the intended IMD 104. However, where the external device 102 has selected the IMD 104 from the set of far field responses and responds by providing the proximity communication 724 that does satisfy the challenge by the intended IMD 104 at the query operation 726, then the external device 102 and the IMD 104 will both continue the far field communication session via subsequent far field communications 730 until the time for the next challenge by the IMD 104 arrives. Upon satisfying the first challenge by the IMD 104, the external device 102 may then cease attempting to satisfy any remaining challenges of other responding IMDs, and those IMDs ignore subsequent communications until the discovery process of FIG. 7 re-starts.

Figure 8:
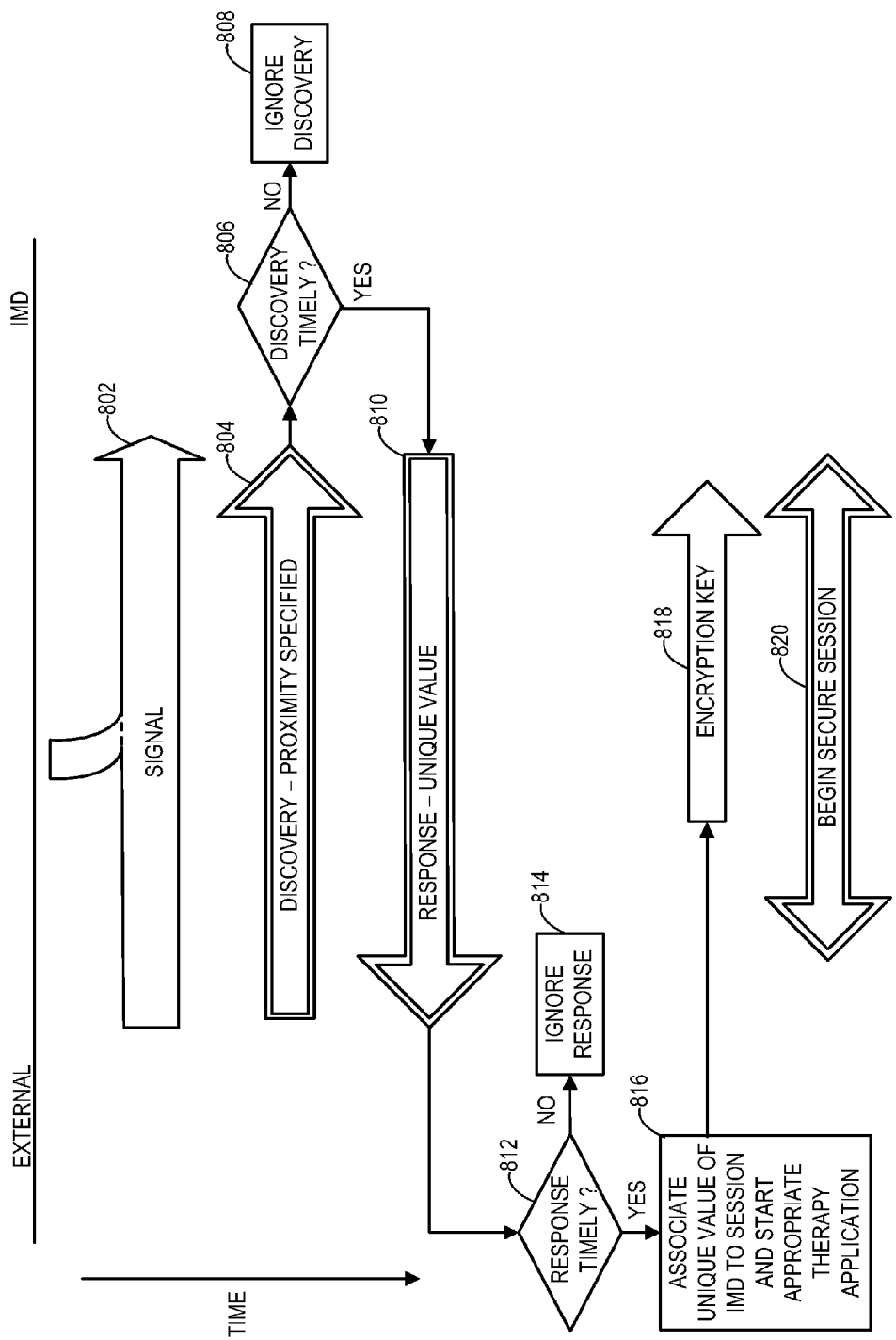
FIG. 8 shows a fifth example of a procedure to establish a far field communication session where an encryption key is exchanged through a proximity communication.

FIG. 8 shows a fifth example of a procedure to establish a far field communication session. In this particular example, the external device 102 relies upon the uniqueness of an encryption key for the secure far field session with the IMD 104 together with the security of the proximity communication as a manner of confirming that the intended IMD 104 has been selected for the far field communication.

Initially, the external device 102 provides a proximity communication 802 in the form of a signal. As discussed above, the proximity communication 802 may be provided by a third party such as the clinician acting at the request of the external device 102 such as to pass a magnet nearby the IMD 104 to provide a form of the proximity communication 802. In either case, this signal may be simple in terms of carrying no data but merely being on or off. Alternatively, this signal of the proximity communication 802 from the external device 102 may be more sophisticated including the ability to carry data. In either case, the IMD 104 may or may not have the ability to send a return proximity communication.

As with FIG. 5, the proximity communication 802 from the external device 102 may serve one or more purposes. For instance, the proximity communication 802 may serve as a trigger for the IMD 104 to respond to far field communication. Likewise, the proximity communication 802 may serve as a wake-up signal to the far field communication abilities of the IMD 104. Furthermore, in some cases, the proximity communication 802 may provide the encryption key to the IMD 104.

The external device 102 also sends a far field discovery communication 804. This far field discovery communication 804 may occur at some point shortly after the proximity communication 802, particularly in examples where the proximity communication 802 serves as a wake-up signal to the far field communication abilities of the IMD 104. The far field discovery communication 804 may occur shortly before or during the proximity communication 802, particularly in examples where the far field communication abilities of the IMD 104 are already functioning prior to the proximity communication 802.

The far field discovery communication 804 serves as an inquiry to all IMDs within range and triggers the receiving IMDs to provide a response that identifies the IMD such as by including a value unique to the IMD 104 in the response to the discovery. In one example, the far field discovery communication 804 specifies a condition for responding. The condition may be that the IMD responds only if the IMD is receiving the far field discovery communication 804 within a predefined time relative to receiving the proximity communication. In one example, the predefined time may be zero, such that the IMD must receive the proximity communication 802 at the time the far field discovery communication 804 is received in order to provide a response.

This condition may be specified by setting a bit value within the discovery request, where the predefined time is preconfigured within the logic of the IMD 104. This condition may alternatively be specified in a more complex manner such as by indicating the predefined amount of time within the request.

In another example, the criteria for responding are preconfigured within the IMD 104. So, in this case, the far field discovery communication 804 may omit any conditions, and the external device 102 may rely on the IMDs that receive the far field discovery communication 804 to properly determine whether to respond based upon the preconfiguration.

In this example, the IMD 104 detects whether the far field discovery communication has arrived within the predefined amount of time relative to receiving the proximity communication 802 at a query operation 806. For those IMDs where no proximity communication 802 has been received or has been received such that the far field discovery communication 804 is outside of the allowed window of time, the far field discovery communication 804 is ignored at an operation 808. For the intended IMD 104, the proximity communication 802 is received and the far field discovery communication arrives within the predefined time relative to the proximity communication 802 so that a far field response communication 810 is returned.

The far field response communication 810 may specify the value that is unique to the IMD 104. The external device 102 may then utilize this unique value to establish a communication session with the IMD 104. However, there is the possibility that multiple IMDs provide a response in this example as well. These responding devices may include the intended IMD 104 as well as the other nearby IMDs who may have also had a proximity signal from other external devices present at the appropriate time relative to the far field discovery communication 804 from the external device 102. In that case, the external device 102 may not determine which IMD 104 is the correct one from the far field responses alone. The external device 102 may instead rely on an exchange of a unique encryption key via a proximity communication.

In this example, the key encryption procedure may be provided by the external device 102 entering into a communication session with a selected one of the responding IMDs. The choice of IMD may be based on time the response was received, strength of the response signal, a random selection, and the like. The external device 102 then attempts to exchange the encryption key via a proximity communication and then begin far field communications using the key. If far field communications fail, the external device 102 then starts a session with the next selected responding IMD to attempt to exchange the encryption key and then begin far field communications. As an alternative, the exchange of the key may be provided followed by the external device 102 entering into separate and simultaneous far field communication sessions with all of the responding IMDs. The external device 102 then attempts to communicate using data encrypted by the encryption key via the far field communication session with each one where sessions with failed far field communication attempts terminate and the session with the successful far field communication proceeds.

When choosing whether to respond to any one of the received responses by establishing a far field communication session, the external device 102 may detect whether each response is timely at a query operation 812 and ignore the response at an operation 814 if not. The external device 102 may then proceed to setup the secure far field communication session(s) for the chosen response or alternatively for each of the responses.

The external device 102 may proceed to associate the unique value of the IMD received in the response to a given far field communication session at an association operation 816 and then send a proximity communication 818 that includes the encryption key. The external device 102 may also then execute the appropriate therapy program automatically based on the value that is unique to the IMD 104 where the external device 102 stores associations of such values to therapy applications.

The external device 102 may then begin sending secure far field communications 818. The external device 102 may communicate during the session by using the unique value of the external device 102 of which the IMD of the session has been made aware via a far field communication to identify the sender of transmissions and/or using the unique value of the IMD of the session to identify the intended recipient of transmissions. Likewise, the IMD of the session may communicate during the session by using the unique value of the IMD of the session of which the external device 102 is aware to identify the sender of transmissions and/or using the unique value of the external device 102 to identify the intended recipient of transmissions.

Upon starting the communication session(s), the IMD of a session in this particular example begins detecting whether any incoming communications can be decrypted. Because the intended IMD 104 is receiving proximity communications from the external device 102, the intended IMD 104 will receive the proximity communication 818 that includes the encryption key regardless of whether the external device 102 is attempting to communicate with the IMD 104 or with another nearby IMD.

In one example where the external device 102 is proceeding with one secure far field session at a time, the external device 102 may provide the proximity communication 818 before each attempt at a secure far field communication session. In that case, if the IMD 104 has yet to receive a secure far field communication from the external device 102 because it is not yet the turn of the IMD 104, then the IMD 104 may simply ignore the proximity communication 818 after a timeout period. In another example where the external device 102 is proceeding with one secure far field session at a time, the external device 102 may provide the proximity communication 818 a single time and then rely on the intended IMD 104 to retain the encryption key until it is the turn of the intended IMD 104 to begin secure far field communications. Furthermore, in that case the key exchange may be provided at the initial proximity communication 802 as opposed to providing the proximity communication 818.

A secure far field communication attempt being sent by the external device 102 may be addressed to another nearby IMD. This other nearby IMD that has been incorrectly selected by the external device 102 has not received the proximity communication 818 that includes the encryption key because this other nearby IMD is not within range of the proximity communication 818. Thus, this other nearby IMD will not be able to decrypt the secure far field communication attempt. As a result, the other nearby IMD will not respond which terminates the session with that other IMD. This other IMD may then wait for the discovery process of FIG. 8 re-starts with another proximity communication 802 and far field discovery communication 804.

In the event the external device 102 has not successfully established secure far field communications with the IMD 104, the external device 102 will need to re-attempt to discover, select, and establish a session with the intended IMD 104. However, where the external device 102 has selected the IMD 104 from the set of far field responses and responds by providing the proximity communication 818, then the external device 102 and the IMD 104 will both begin exchanging secure far field communications 820.

FIG. 9 shows a sixth example of a procedure to establish a far field communication session. In this particular example, the external device 102 relies upon a strength of far field signal between the external device 102 and the responding IMDs as a manner of confirming that the intended IMD 104 has been selected for the far field communication. This may be a valid manner of confirmation considering that the odds of a nearby IMD receiving a proximity communication at the proper time in order to trigger the response to the discovery message coupled with a strength of signal for that nearby IMD being stronger than the strength of the intended IMD 104 are relatively low.

The signal strength of interest may vary from one example to the next. For instance, the signal strength may be from the perspective of the IMD for a far field communication sent by the external device 102 such as a discovery message. That signal strength may be reported by the IMD in a response to the discovery message. The signal strength may be from the perspective of the external device 102 for a far field communication sent by the IMD such as the response to the discovery message. The signal strength may be based on a combination of these values and may be based on other far field communications between the external device 102 and the IMD as well.

Initially, the external device 102 provides a proximity communication 902 in the form of a signal. As discussed above, the proximity communication 902 may be provided by a third party such as the clinician acting at the request of the external device 102 such as to pass a magnet nearby the IMD 104 to provide a form of the proximity communication 902. In either case, this signal may be simple in terms of carrying no data but merely being on or off. Alternatively, this signal of the proximity communication 902 from the external device 102 may be more sophisticated including the ability to carry data. In either case, the IMD 104 may or may not have the ability to send a return proximity communication.

As with FIG. 5, the proximity communication 902 from the external device 102 may serve one or more purposes. For instance, the proximity communication 902 may serve as a trigger for the IMD 104 to respond to far field communication. Likewise, the proximity communication 902 may serve as a wake-up signal to the far field communication abilities of the IMD 104.

The external device 102 also sends a far field discovery communication 904. This far field discovery communication 904 may occur at some point shortly after the proximity communication 902, particularly in examples where the proximity communication 902 serves as a wake-up signal to the far field communication abilities of the IMD 104. The far field discovery communication 904 may occur shortly before or during the proximity communication 902, particularly in examples where the far field communication abilities of the IMD 104 are already functioning prior to the proximity communication 902.

The far field discovery communication 904 serves as an inquiry to all IMDs within range and triggers the receiving IMDs to provide a response that identifies the IMD such as by including a value unique to the IMD 104 in the response to the discovery. In one example, the far field discovery communication 904 specifies a condition for responding. The condition may be that the IMD responds only if the IMD is receiving the far field discovery communication 904 within a predefined time relative to receiving the proximity communication. In one example, the predefined time may be zero, such that the IMD must receive the proximity communication 902 at the time the far field discovery communication 904 is received in order to provide a response.

This condition may be specified by setting a bit value within the discovery request, where the predefined time is preconfigured within the logic of the IMD 104. This condition may alternatively be specified in a more complex manner such as by indicating the predefined amount of time within the request.

In another example, the criteria for responding are preconfigured within the IMD 104. So, in this case, the far field discovery communication 904 may omit any conditions, and the external device 102 may rely on the IMDs that receive the far field discovery communication 904 to properly determine whether to respond based upon the preconfiguration.

In this example, the IMD 104 detects whether the far field discovery communication has arrived within the predefined amount of time relative to receiving the proximity communication 902 at a query operation 906. For those IMDs where no proximity communication 902 has been received or has been received such that the far field discovery communication 904 is outside of the allowed window of time, the far field discovery communication 904 is ignored at an operation 908. For the intended IMD 104, the proximity communication 902 is received and the far field discovery communication arrives within the predefined time relative to the proximity communication 902 so that a far field response communication 910 is returned.

The far field response communication 910 may specify the value that is unique to the IMD 104. The external device 102 may then utilize this unique value to establish a communication session with the IMD 104. The far field response communication 910 may also specify a signal strength such as that as detected by the responding IMD for the far field discovery communication 904. Additionally or alternatively, the external device 102 may collect the signal strength of the far field response communication 910. There is the possibility that multiple IMDs provide a response in this example as well, and the external device 102 collects signal strength information for each response. These responding devices may include the intended IMD 104 as well as the other nearby IMDs who may have also had a proximity signal from other external devices present at the appropriate time relative to the far field discovery communication 904 from the external device 102. In that case, the external device 102 may not determine which IMD 104 is the correct one from the far field responses alone. The external device 102 may instead rely on the collected signal strength related to the responding IMDs.

When choosing whether to respond to any one of the received responses by establishing a far field communication session, the external device 102 may detect whether each response is timely at a query operation 912 and ignore the response at an operation 914 if not. As stated above, the external device 102 collects the signal strength information for each of the responding IMDs. The external device 102 may continue to receive and collect the signal strength information until determining at a query operation 916 that a response period has ended. The external device 102 may then determine for each responding IMD whether that IMD is associated with the strongest signal at a query operation 918. These operations are iterated for to account for each IMD 104.

If a responding IMD is not associated with the strongest signal, then the external device ignores the response at the operation 914. However, for the responding IMD that is associated with the strongest signal, the external device 102 proceeds to associate the unique value of that responding IMD that was received in the far field response communication 910 to the far field communication session at an association operation 920. The external device 102 may also then execute the appropriate therapy program automatically based on the value that is unique to the IMD 104 where the external device 102 stores associations of such values to therapy applications.

The external device 102 may then communicate during the session by using the unique value of the external device 102 of which the IMD 104 has been made aware via a far field communication to identify the sender of transmissions and/or using the unique value of the IMD 104 to identify the intended recipient of transmissions. Likewise, the IMD 104 may communicate during the session by using the unique value of the IMD 104 of which the external device 102 is aware to identify the sender of transmissions and/or using the unique value of the external device 102 to identify the intended recipient of transmissions.

To further ensure that the IMD that has been selected based on signal strength is the intended IMD, other techniques may then be performed. For instance, a challenge procedure initiated by the external device 102 as in FIG. 6 or initiated by the IMD 104 as in FIG. 7 may be conducted. As another example, the encryption key may be exchanged via proximity communication as in FIG. 8.

Regardless of whether a procedure similar to that of FIG. 8 is used for further confirmation, the session may be made secure by encrypting the information with an encryption key. This encryption key may have been generated for the session by the external device 102 and included in a far field communication so that the IMD 104 obtains the key. As one example, the key may be exchanged by using a low power radio frequency communication to minimize the range. Furthermore, the IMD 104 may provide the key for the secure session rather than receiving the key from the external device 102. To the extent the devices have a capable manner of using more complex proximity communications, the key may be exchanged through proximity communication rather than through far field communication as discussed above for FIG. 8.

With regard to FIGS. 4-9, it will be appreciated that the roles of the external device 102 and IMD 104 may be reversed. As one example, in relation to FIG. 5, the external device may issue the challenge to the IMD, and the IMD 104 may have the ability to send proximity communications while the external device 102 receives them. As another example, in relation to FIG. 6, the IMD 104 may request that the external device 102 issue a challenge that the IMD 104 then responds to via a proximity communication. As yet another example, in relation to FIG. 7, the external device 102 may periodically challenge the IMD 104 which responds via a proximity communication.

While embodiments have been particularly shown and described, it will be understood by those skilled in the art that various other changes in the form and details may be made therein without departing from the spirit and scope of the invention.

What is claimed is:

1. A method of establishing communication between an external device and at least one of a plurality of implantable medical devices (IMDs), comprising:
   monitoring, with each of the plurality of IMDs, for a proximity communication from the external device that is unaware of an identifier value that is unique to each of the plurality of IMDs, respectively;
   receiving, with the at least one of the plurality of IMDs, the proximity communication from the external device, the proximity communication comprising a value that is unique to the external device;
   after receiving the proximity communication with the at least one of the plurality of IMDs, monitoring, with IMDs that received the proximity communication, for a far field discovery communication, the far field discovery communication being a far field inquiry from the external device to all of the plurality of implantable medical devices within communication range of the external device;
   receiving the far field discovery communication with the IMDs that received the proximity communication and that are in the communication range with the external device;
   responding, with the IMDs that received the proximity communication and that received the far field discovery communication, to the far field discovery communication by transmitting a far field response communication, the far field response communication comprising the value that is unique to the external device and the identifier value that is unique to each respective IMD that received the proximity communication and that received the far field discovery communication; and
   exchanging information with the external device using far field communication by transmitting, with the IMDs that received the proximity communication and that received the far field discovery communication, the information in conjunction with the identifier value that is unique to each respective IMD.

2. The method of claim 1, wherein the proximity communication from the external device further includes an encryption key.

3. The method of claim 2, wherein exchanging information with the external device using far field communication comprises encrypting the information with the encryption key.

4. The method of claim 1, wherein exchanging information with the external device further comprises using far field communication by receiving the information in conjunction with the value that is unique to the external device.

5. A system for establishing communication, comprising:
   an external device and an implantable medical device, wherein the implantable medical device is configured to:
      monitor for a proximity communication from the external device that is unaware of an identifier value that is unique to the implantable medical device;
      receive the proximity communication from the external device, the proximity communication comprising a value that is unique to the external device;
      after receiving the proximity communication, monitor for a far field discovery communication, the far field discovery communication being a far field inquiry from the external device to all implantable medical devices within communication range of the external device;
      receive the far field discovery communication;
      respond to the far field discovery communication by transmitting a far field response communication, the far field response communication comprising the identifier value that is unique to the implantable medical device and the value that is unique to the external device; and
      exchange information with the external device using far field communication by transmitting the information in conjunction with the identifier value that is unique to the implantable medical device.

6. The system of claim 5, wherein the proximity communication from the external device further includes an encryption key.

7. The system of claim 6, wherein the implantable medical device exchanges information with the external device using far field communication by encrypting the information with the encryption key.

8. The system of claim 5, wherein implantable medical device exchanges information with the external device using far field communication by receiving the information in conjunction with the value that is unique to the external device.

* * * * *